United States Patent [19]

Gay, Jr.

[11] Patent Number: 5,334,207
[45] Date of Patent: Aug. 2, 1994

[54] LASER ANGIOPLASTY DEVICE WITH MAGNETIC DIRECTION CONTROL

[75] Inventor: Lindell W. Gay, Jr., Norman, Okla.

[73] Assignee: Allen E. Coles, Oklahoma City, Okla.

[21] Appl. No.: 36,768

[22] Filed: Mar. 25, 1993

[51] Int. Cl.⁵ .............................................. A61B 17/36
[52] U.S. Cl. .......................................... 606/7; 606/15; 606/16; 604/95
[58] Field of Search ................. 606/7, 10–16; 128/395, 397, 398, 656–14 658, 4, 6; 604/95, 96, 280, 281, 211; 607/88, 89

[56] References Cited

U.S. PATENT DOCUMENTS

| | | | |
|---|---|---|---|
| 3,674,014 | 7/1972 | Tillander | 128/2.05 R |
| 4,483,341 | 11/1984 | Witteles | 606/21 |
| 4,758,222 | 7/1988 | McCoy | 604/95 |
| 4,784,133 | 11/1988 | Mackin | 606/7 |
| 4,826,087 | 5/1989 | Chinery | 239/551 |
| 4,848,336 | 7/1989 | Fox et al. | 606/7 |
| 4,913,142 | 4/1990 | Kittrell et al. | 606/7 |
| 4,934,340 | 6/1990 | Ebling | 128/6 |

OTHER PUBLICATIONS

Article "Design of an Endoscopic Carrier with Complete Directional Control," Lachiver and Seufert, Annals of Biomedical Engineering, vol. 7, No. 3-4, pp. 345-355, 1979.

Article, "Selective Angiography with a Catheter Guided by a Magnet," Tillander, *IEEE Transactions on Magnetion*, vol. MAG-6, No. 2, Jun. 1970.

Primary Examiner—Stephen C. Pellegrino
Assistant Examiner—M. Peffley
Attorney, Agent, or Firm—Dunlap, Codding & Lee

[57] ABSTRACT

A laser angioplasty device having magnetic steerability and forward imaging capability. The device includes a probe, an electromagnetic control system coupled with the probe, a fluid injection system, an imaging system, a laser source and a balloon system. A laser fiber and a plurality of control wires, fluid injection tubes, balloon tubes, light-emitting optical fibers and imaging optical fibers extend throughout the length of the probe. A magnetized sleeve is journaled around a portion of the laser fiber which protrudes from the tip of the probe. The electromagnetic control system includes a joystick, a plurality of electromagnets and an electronic circuit for varying the magnetic fields of the electromagnets in response to the position of the joystick. The magnetic fields are induced into the control wires of the probe to influence the magnetized sleeve for steering and aiming the tip of the laser fiber.

26 Claims, 6 Drawing Sheets

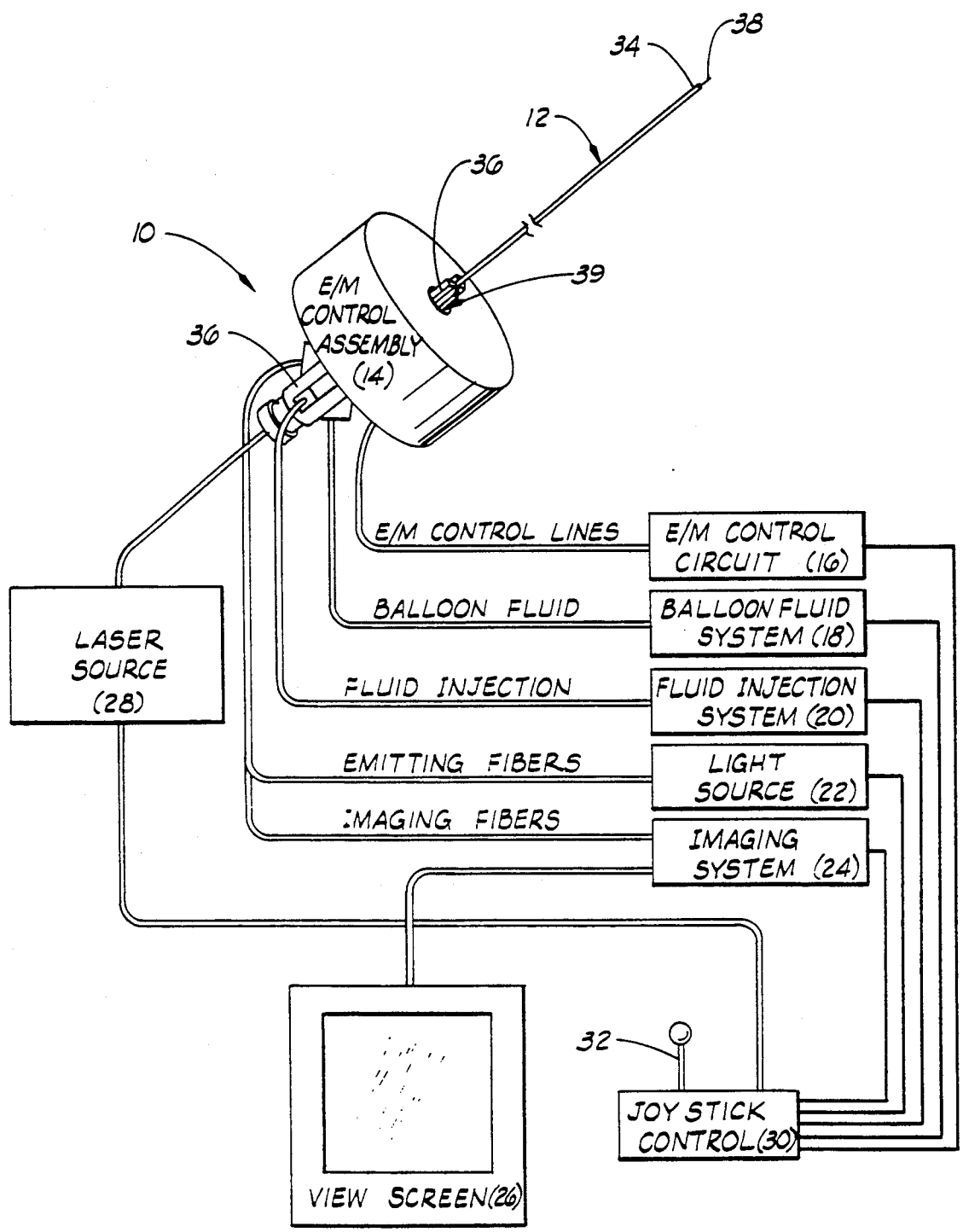

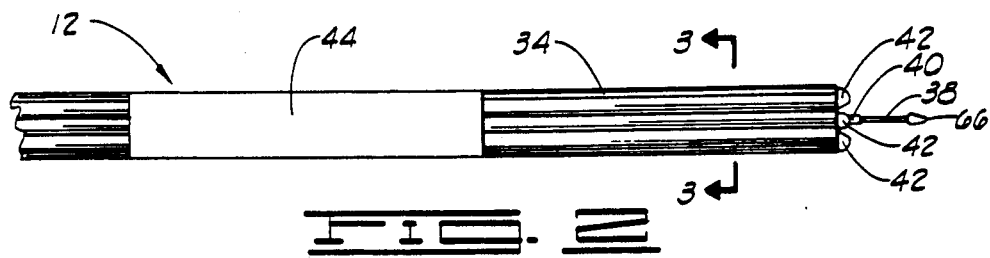
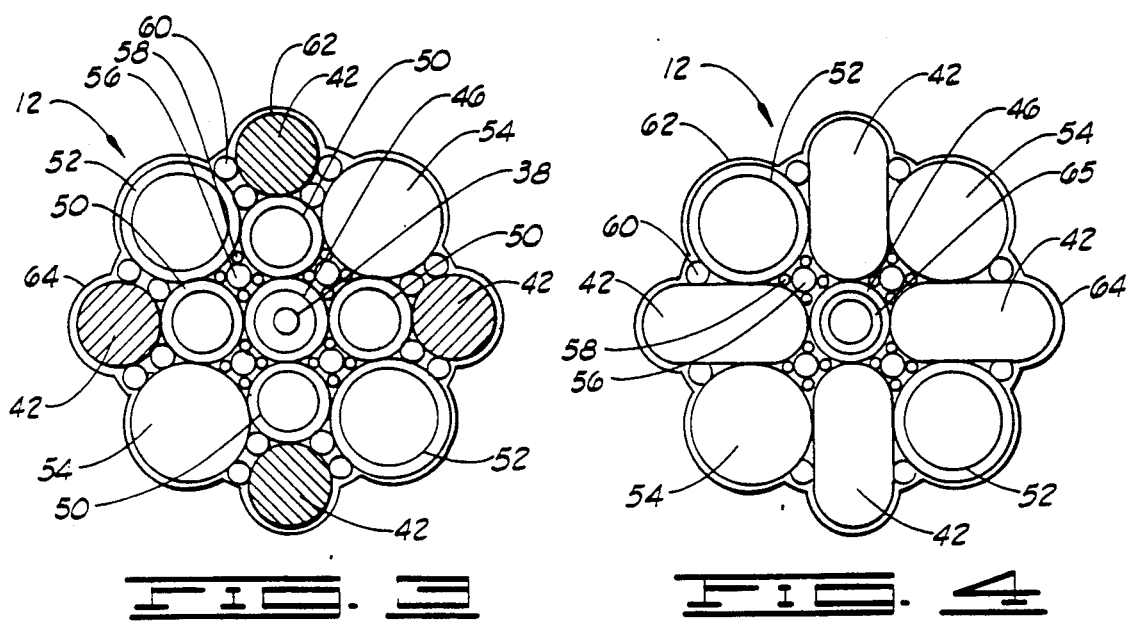
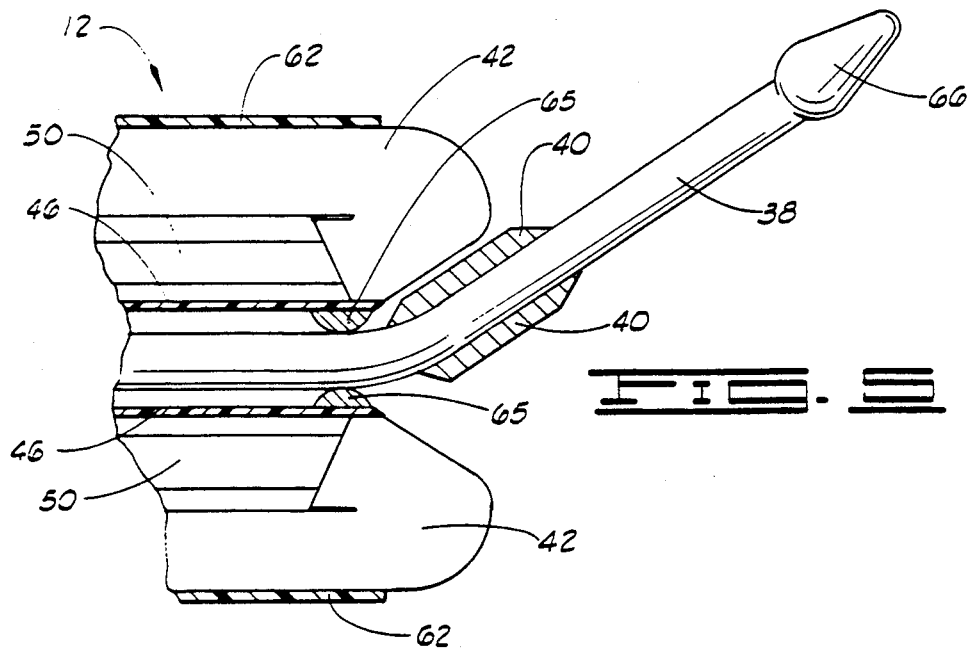

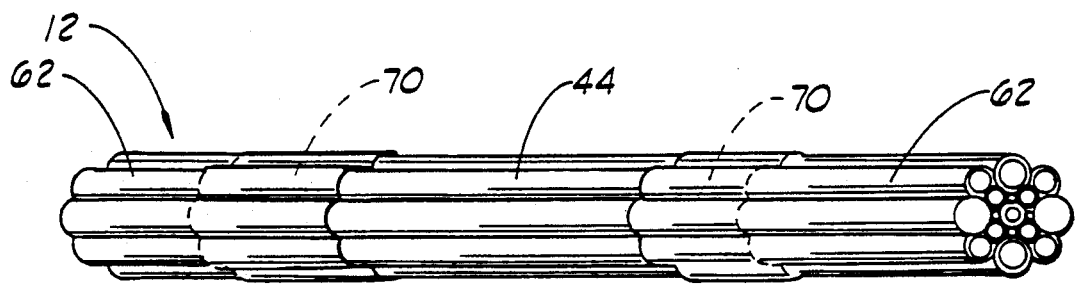
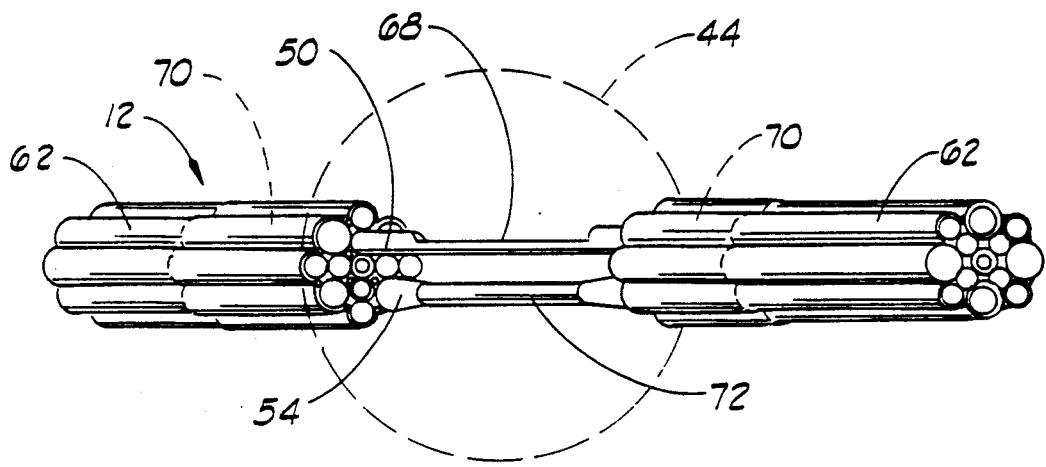
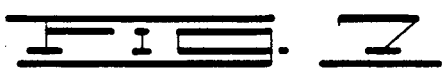
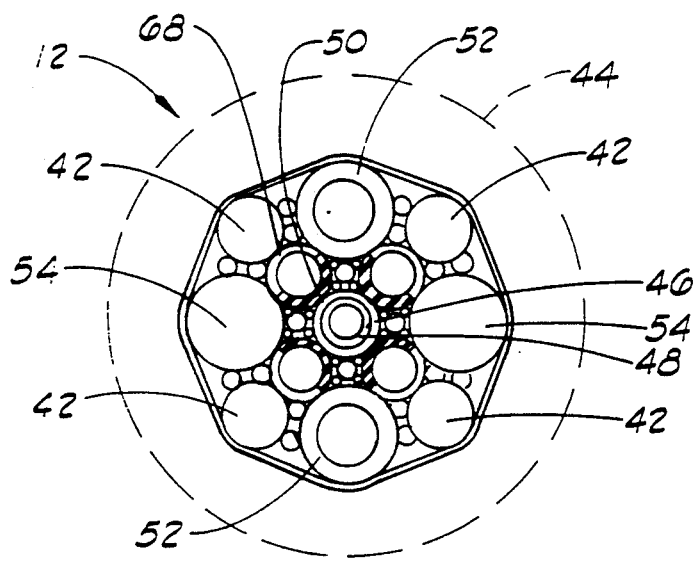
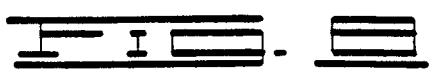

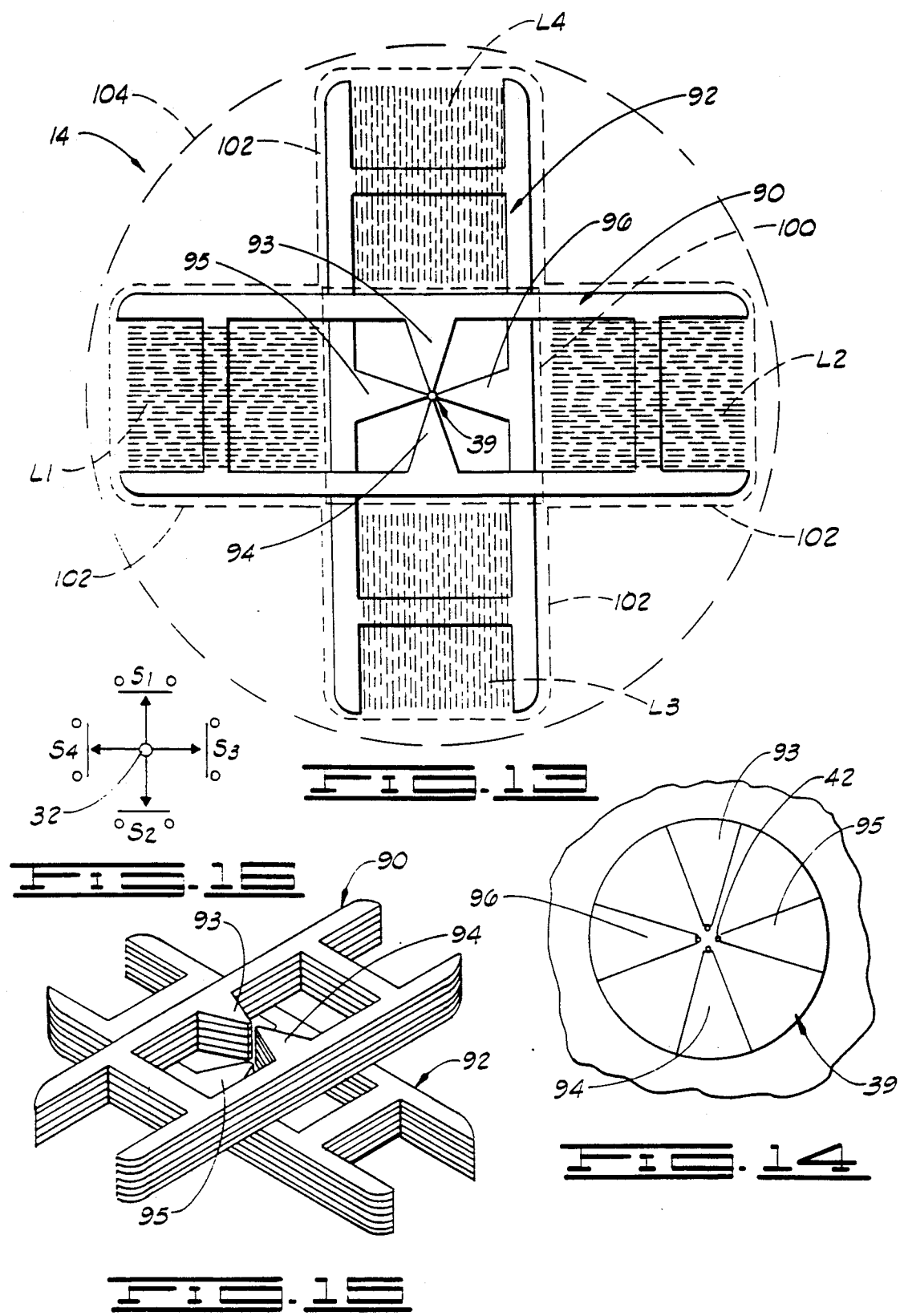

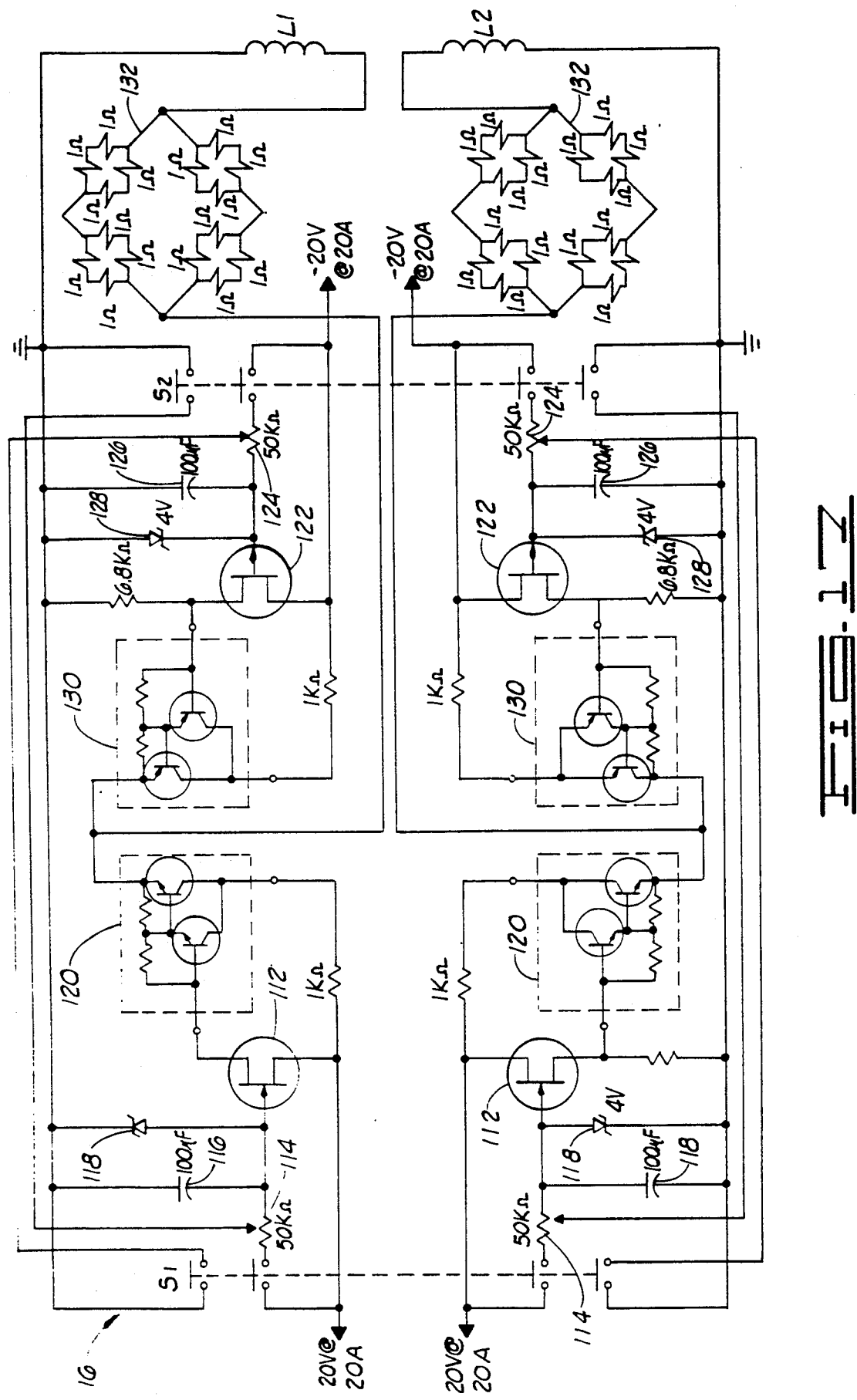

LASER ANGIOPLASTY DEVICE WITH MAGNETIC DIRECTION CONTROL

BACKGROUND OF THE INVENTION

1. Field of the Invention

The present invention relates generally to angioplasty and catheterization devices, and particularly to such devices using laser technology to remove occlusions from blood vessels and organs of the body.

2. Description of Related Axle

Angioplasty, the repair of a blood vessel, may be performed in several ways. Angioplasty may take the form of surgery to replace the occluded portion of the clogged vessel with either a piece of the patient's own tissue or a prosthetic vessel. This type of angioplasty is relatively difficult to perform and involves considerable trauma to the patient.

In balloon angioplasty, a balloon-tipped catheter is inserted into the clogged blood vessel and the balloon is inflated to expand the passageway of the blood vessel. Balloon angioplasty is not as difficult and traumatic as replacement surgery, but it does not actually remove the occlusion. Thus the vessel walls may return to their occluded position after a short period of time.

Furthermore, balloon angioplasty is an option only where there is a passageway sufficiently open for the insertion of the balloon-tipped catheter. Accordingly, balloon angioplasty cannot be performed in cases where blood vessels have a high degree of occlusion.

At the present, lasers used for angioplasty are steered by a guide wire which is pre-inserted through the clogged area of the vessel with the assistance of x-ray visualization. Unfortunately, this technique is not effective for highly occluded vessels because the occlusion prevents the insertion of the guide wire.

Angioplasty lasers currently in use emit a laser beam having a wavelength in the ultraviolet range. This wavelength produces clean vaporization of tissue in its path with little thermal damage to the surrounding tissue. The catheter tip of such lasers, however, must be in contact with the tissue in order for vaporization to occur. The laser beam has no means of aiming other than the guide wire. Thus the area of vaporization is limited to the size of the lumen produced by the laser.

Finally, the laser catheter in use today follows the guide wire blindly and vaporizes both the atherosclerotic tissue and the normal tissue in its path. With the guide wire technique, there is no capability for visually monitoring and controlling the laser angioplasty procedure as it is being performed.

SUMMARY OF THE INVENTION

The present invention is a laser angioplasty probe having a magnetically controlled tip. The tip is magnetically steered to guide the probe through a vessel to an occlusion in the vessel. Once positioned at the site of the occlusion, the tip is magnetically aimed to direct laser pulses at the occlusion.

A device constructed in accordance with the present invention includes an elongated, flexible probe having a laser fiber surrounded by a plurality of control wires. The laser fiber has an end portion and a laser tip which protrude beyond the control wires. A magnetized sleeve is disposed around the end portion of the laser fiber. A laser source is operatively connected to the laser fiber to emit laser pulses from the laser tip. Art electromagnetic assembly, controlled by an electronic circuit and joystick, are provided to induce magnetic fields in the control wires. In response to movement of the joystick, the magnetic fields of the control wires influence movement of the magnetized sleeve to aim the laser tip.

One object of the present invention is to provide a laser angioplasty probe which can be steered and aimed in wide range of forward directions after insertion into the occluded vessel.

Another object of the present invention is to provide a laser angioplasty probe for use in blood vessels which are so occluded that laser catheters depending on guide wires are ineffectual.

Yet another object of the present invention is to provide a laser angioplasty probe with angioscopic capability enabling the probe operator to steer the probe within the vessel and aim the laser beam at the occlusion by visual interaction.

Other objects, features and advantages of the present invention are apparent from the following detailed description when read in conjunction with the accompanying drawings and appended claims.

BRIEF DESCRIPTION OF THE DRAWINGS

FIG. 1 is a diagrammatical view of a laser angioplasty device constructed in accordance with the present invention.

FIG. 2 is a side elevation of the probe tip of the laser angioplasty device of FIG. 1.

FIG. 3 is a partly diagrammatical sectional view of the probe tip taken along the lines 3—3 of FIG. 2.

FIG. 4 is a front view of the probe tip. The laser fiber and magnetized sleeve are omitted for clarity of illustration.

FIG. 5 is a partly sectional, partly diagrammatical side view of the probe tip.

FIG. 6 is a partly diagrammatical perspective view of the balloon region of the probe tip of FIG. 2.

FIG. 7 is the same view as FIG. 6, but with a cutaway view of the balloon region.

FIG. 8 is a partly diagrammatical, partly sectional view of the balloon region of the probe tip of FIG. 6.

FIG. 13 is a diagrammatical end view of the electromagnetic assembly of FIG. 1.

FIG. 14 is a partly diagrammatical front view of the probe-receiving aperture of the electro-magnetic assembly of FIG. 13.

FIG. 15 is a diagrammatical perspective view of the cores of the electro-magnetic assembly of FIG. 13.

FIG. 16 is a diagram of the joystick of FIG. 1 illustrating the movement of the joystick.

FIG. 17 is a schematic diagram of the electro-magnetic circuit of FIG. 1.

DETAILED DESCRIPTION OF THE PREFERRED EMBODIMENTS

Figure 9:
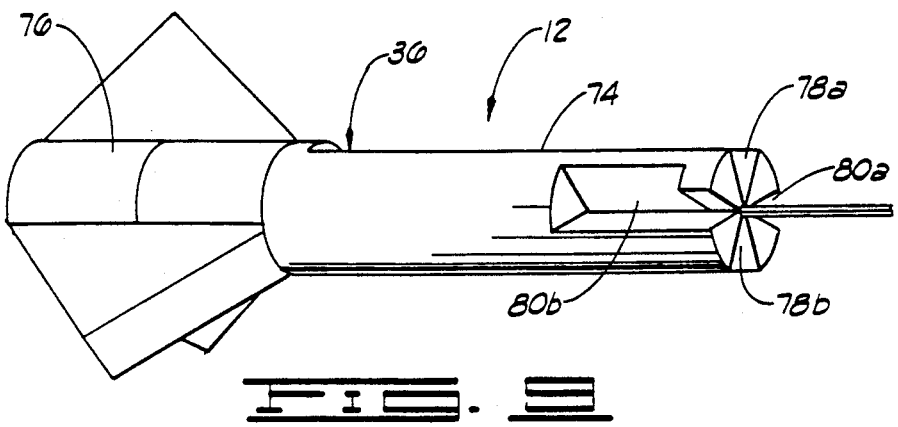
FIG. 9 is a perspective view of the probe coupler of the laser angioplasty device of FIG. 1.

Referring to the drawings in general, and to FIG. 1 in particular, shown therein and designated by the general reference numeral 10 is a laser angioplasty device, which includes a probe 12, an electromagnetic (E/M)

control assembly 14, an electro-magnetic (E/M) control circuit 16, a balloon fluid system 18, a fluid injection system 20, a light source 22, an imaging system 24 with a view screen 26 and a laser source 28.

A control box 30 with a joystick 32 is operatively connected to the E/M control circuit 16, the balloon fluid system 18, the fluid injection system 20, the light source 22, the imaging system 24 and the laser source 28. The joystick 32 is connected to the E/M control circuit 16 to operate the E/M control assembly 14. It should be appreciated that other switches, dials and controls (not shown) are provided on the control box 30 for operating the balloon fluid system 18, the fluid injection system 20, the light source 22, the imaging system 24 and the laser source 28.

The probe 12 is a flexible, elongated structure having a probe tip 34 at one end and a probe coupler 36 at the opposite end. As shown in FIG. 1, the balloon fluid system 18, the fluid injection system 20, the light source 22, the imaging system 24 and the laser source 28 are all connected to the probe 12 through the probe coupler 36. The E/M control assembly 14 has an aperture 39 through which the probe coupler 36 is inserted. The probe tip 34 includes a protruding laser fiber 38 which is journaled through a magnetized sleeve (not visible in FIG. 1).

Typically, the probe 12 is approximately one meter in length and about 0.0988 inches in diameter. These probe 12 dimensions allow the probe 12 to be inserted into a vessel and to reach an occlusion which may be located in almost any vessel of the human body. It should be appreciated, however, that the probe 12 may be made in a wide variety of lengths and diameters.

The probe coupler 36 and the aperture 39 are typically constructed with uniform dimensions, while the insertable portion of the probe 12 may be made in different lengths and effective diameters. In this manner, probes 12 having a wide range of lengths and effective diameters may be utilized with the device 10.

The laser source 28 is operatively connected to the laser fiber 38, which extends throughout the length of the probe 12. The laser source 28 may comprise any of several excimer laser wavelengths, such as 193 nanometers (ArF), 222 nm (KrCl), 248 nm (KrFe), 308 nm (XeCl) or 351 nm (XeF).

The laser source 28 is adapted to be pulsed at a laser pulse durations in the range of 10 to 85 nanoseconds. The laser pulse durations are very important to the proper operation of the device 10. Durations shorter than 10 nanoseconds may not excise the occlusion efficiently and durations longer than 85 nanoseconds may cause thermal damage to the healthy tissue of the occluded vessel.

The laser light produced by the laser source 28 is in the ultra-violet range and is not itself visible on the video monitor 26. In order to see where the laser pulses are aimed, the laser source 28 is adapted to emit a tracer beam as well as the laser pulses. The tracer beam may be a monochromatic light, a high-intensity light or any light which is readily visible in the type of illumination provided by the light source 22.

Equipment known in the art is used for the fluid injection system 20 to flush blood out of the vessel between the probe tip 34 and the occlusion. Typically, the fluid injection system 20 includes a pump, reservoir, connecting tubes and controls. The fluid used may be saline or any other sterile, substantially transparent solution.

The imaging system 24 is similar to equipment used in conventional endoscopes and is capable of converting images from optical fibers to visually perceptive images on the video monitor 26. A path of imaging fibers extends all the way from the probe tip 34 to the imaging system 24 to provide visual images of the interior of the vessel from the perspective of the probe tip 34.

In order to provide light within the vessel, the light source 22 is connected to a bundle of light-emitting optical fibers which extend substantially throughout the length of the probe 12. The light utilized may be a high-intensity halogen light or a laser light. Although an acceptable light may be in various ranges of the color spectrum, visibility within the vessel is enhanced if a substantial component of the light is white light.

It should be appreciated that the imaging fibers and the light-emitting fibers are typically cladded optical fibers. The cladding improves the flexibility of the imaging and light-emitting fibers.

The balloon fluid system 18 is similar the fluid injection system 20. A plurality of balloon fluid tubes connect the balloon fluid system 18 to the probe coupler 36 and balloon tubes also run the length of the probe 12. Although another suitable fluid could be used, a saline solution is typically pumped into the probe 12 to inflate the balloon (not shown in FIG. 1). The balloon fluid system 18 is also capable of placing a vacuum on the balloon fluid tubes to draw fluid out of the balloon to deflate the balloon.

Turning now to FIGS. 2 through 5, the detailed structures of the probe 12 and probe tip 34 are illustrated therein. As shown in FIGS. 2 and 5, the laser fiber 38 protrudes from the end of the probe 12 and is journaled through the magnetized sleeve 40. The diameter of the probe 12 is in the range of 0.0984 inches, while the diameter of the laser fiber 38 is typically about 300 microns.

The laser fiber 38 has an outer diameter of approximately 300 microns and typically comprises a 250-micron polymethyl methacrylate core covered by a 50-micron "TEFLON" cladding. As an alternative material, the laser fiber 38 may be made of silica. The cladding substantially enhances the flexibility of the laser fiber 38. In the case of a silica laser fiber 38, the cladding is essential to prevent the silica from breaking off within the vessel.

Four control wires 42 also protrude from the end of the probe 12, but not as far as the laser fiber 38. It should be appreciated that only three of the control wires 42 are visible in FIG. 2. The diameter of each of the control wires 42 is on the order of 0.016 inches.

At approximately one inch from its end, the probe 12 has a circumferential balloon 44, typically made of urethane, polyurethane diisocyanate, isobutylene-isoprene or a similar substance. The total length of the balloon 44 is about 0.5 inches. With the exception of the balloon 44 region, the probe 12 has a uniform structure from the probe tip 34 all the way back to the probe coupler 36.

With reference to FIG. 3, the basic internal structure of the probe 12 is shown therein. For clarity of illustration, the laser fiber 38 and magnetized sleeve 40 are not shown in FIG. 3.

At the center of the probe 12 is a laser tube 46, which contains the laser fiber 38. The laser tube 46 typically has an inner diameter of about 400 microns and an outer diameter of approximately 500 microns. The laser tube 46 may be made of "TEFLON", nylon or any material having characteristics similar to "TEFLON" and nylon.

Four balloon injection tubes 50 are positioned around the laser tube 46. Each balloon injection tube 50 has an inner diameter of about 400 microns and an outer diameter of approximately 500 microns. Nylon or a substance similar to nylon is a suitable construction material for the balloon injection tubes 50.

To the outside of the balloon injection tubes 50, two fluid injection tubes 52 are positioned across from one another in the probe 12. Like the balloon injection tubes 50, the fluid injection tubes 52 are typically constructed of nylon or a similar material. The inner and outer diameters of the fluid injection tubes 52, however, are about 600 microns and 700 microns, respectively.

Two imaging fibers 54 are also located outside the balloon injection tubes 50 and are located across from one another within the probe 12. The imaging fibers 54 are approximately 700 microns in diameter and are constructed of polymethyl methacrylate or silica.

The four control wires 42 are positioned at about ninety-degree intervals in the probe 12. Each control wire 42 is positioned between one of the fluid injection tubes 52 and one of the imaging fibers 54. Each control wire 42 is approximately 0.016 inches in diameter and may be made of any ferromagnetic material.

For efficient operation, the control wires 42 should comprise a substance having extremely high relative magnetic permeability, such as "SUPERMALLOY." "SUPERMALLOY" is an alloy of about 79% Nickel and 16% Iron, which may have a relative magnetic permeability, or $\mu_r$, curve ranging from 10,000 to 1,000,000 and low magnetic losses.

The voids between the laser tube 46, the balloon injection tubes 50, the fluid injection tubes 52 and the control wires 42 are substantially filled by light-emitting fibers. In order to fit properly within the probe 12, three different diameters of light-emitting fibers may be used.

Four 150-micron diameter light-emitting fibers are positioned around the laser tube 46. As shown in FIG. 3, one of the 150-micron diameter light-emitting fibers is designated by reference numeral 56 and is generally representative of the 150-micron diameter light-emitting fibers.

Each of the 150-micron fibers 56 is, in turn, surrounded by four 100-micron diameter light-emitting fibers. One of the 100-micron diameter light-emitting fibers is designated by reference numeral 58 and is generally representative of the 100-micron light-emitting fibers.

The third size of light-emitting fibers is 130 microns in diameter. A pair of the 130-micron light-emitting fibers is positioned between each control wire 42 and the neighboring fluid injection tube 52 and between each control wire 42 and the nearby imaging fiber 54. In FIG. 3, one pair of the 130-micron diameter light-emitting fibers is designated by reference numeral 60 and is generally representative of the 130-micron light-emitting fibers within the probe 12.

The light-emitting fibers 56, 58 and 60 are typically constructed of polystyrene. Silica, polymethyl methacrylate or similar materials may also be used for the light-emitting fibers 56, 58 and 60.

An outer sheath 62 contains the control wires 42, laser tube 46, balloon tubes 50, fluid injection tubes 52, imaging fibers 54, and light-emitting fibers 56, 58 and 60 of the probe 12. Typically, the sheath 62 comprises a 2.5 millimeter heat-shrinkable "TEFLON" tube which is formed around the inner components of the probe 12 through a heat-shrinking process.

As shown in FIG. 3, the shape of the outer periphery of the probe 12 has eight uniformly spaced rounded runners which substantially extend from the end of the probe 12 to the probe coupler 36. The eight rounded runners are formed by shrinking the outer sheath 62 onto the four control wires 42, the two fluid injection tubes 52 and the two imaging fibers 54. One of the rounded runners is designated by reference numeral 64 and is generally representative of the rounded runners of the probe 12.

With this construction, the runners 64 are basically the only portion of the probe 12 to make contact with the inner walls of the vessel and the overall frictional contact of the outer sheath 62 with the inner wall of the vessel is thereby reduced. Thus insertion of the probe 12 into the vessel is facilitated by making the outer sheath 62 of "TEFLON" which has a low coefficient of friction, and by shaping the outer periphery of the probe 12 to have the rounded runners 64.

It should be appreciated that the structure just described is present throughout almost the entire length of the probe 12 from the probe coupler 36 to the probe tip 34. At the end of the probe tip 34 and within the balloon 44 region, however, the structure of the probe 12 is somewhat different.

As illustrated by FIGS. 4 and 5, the control wires 42 are bent over at the end of the probe tip 34 to lie at an angle of about 45 degrees to the laser tube 46. This construction allows the control wires 42 to exert a high degree of magnetic influence on the magnetized sleeve 40 around the laser fiber 38.

Although the magnetized sleeve 40 may be made of any ferromagnetic material, it typically comprises samarium cobalt. In order to be moved magnetically, the magnetized sleeve 40 is radially magnetized. That is, the outer periphery of the magnetized sleeve 40 has one magnetic polarity, such as "north," and the inner periphery of the magnetized sleeve 40 has the opposite magnetic polarity, such as "south."

To aim the laser fiber 38 as shown in FIG. 5, the upper control wire 42 has a magnetic polarity opposite to that of the outer periphery of the magnetized sleeve 40 and attracts the magnetized sleeve 40. Conversely, the lower control wire 42 has the same magnetic polarity as the outer periphery of the magnetized sleeve 40 and repels the magnetized sleeve 40. It should be appreciated that the other two control wires 42 (not shown in FIG. 5) may at the same time exert magnetic influence on the magnetized sleeve 40 from their locations.

An annular base 65 may be attached to the inner periphery of the laser tube 46 near the end of the laser tube 46. The annular base 65 may comprise samarium cobalt or stainless steel or any ferromagnetic material.

The annular base 65 may be permanently magnetized to have a radial magnetic polarity which is opposite to that of the magnetized sleeve 40. In other words, if the inner periphery of the magnetized sleeve 40 has a "north" polarity, then the inner periphery of the annular base 65 would have a "south" polarity. Similarly, if the outer periphery of the magnetized sleeve 40 has a "south" polarity, then the outer periphery of the annular base 65 would have a "north" polarity. With this magnetization, the annular base 65 and the magnetized sleeve 40 have a magnetic attraction which enhances the stability of the laser fiber 38 at the end of the probe 12.

It should be appreciated that the annular base 65 and the magnetized sleeve 40 are not allowed to contact one another. The end of the laser tube 46 extends beyond the annular base 65 and beveled to mate with the magnetized sleeve 40. When the laser fiber 38 is directed straight ahead, the beveled end of the magnetized sleeve 40 rests entirely on the beveled end of the laser tube 46. When the laser fiber 38 is bent, as shown in FIG. 5, the magnetized sleeve 40 may not contact the beveled end of the laser tube 46 at all.

As illustrated by FIG. 5, the laser fiber 38 has a bulbous tip 66. The size of the bulbous tip 66 should be large enough to prevent the magnetized sleeve 40 from sliding off the laser fiber 38. The bulbous tip 66 is tapered toward its end in order to direct laser pulses more effectively.

In order to insert the probe 12 into the vessel, the probe 12 must be comparable in cross-sectional size to the vessel near the occlusion. Of course, if the probe 12 is too large it cannot be inserted into the vessel. Conversely, too much space between the probe 12 and the walls of the vessel may also cause problems. First, by being loosely situated within the vessel, the probe tip 34 may not be completely stationary during the laser excision of the occlusion. Secondly, blood may flow between the probe 12 and the inner wall of the vessel and create too much opacity for effective visual imaging.

The balloon 44 solves the difficulties caused by a loosely situated probe tip 34. By inflating the balloon 44 to engage the inner walls of the vessel, the probe tip 34 is stabilized within the vessel.

As shown in FIG. 6, the balloon 44 has ends 70 which are tucked under the outer sheath 62. Both ends 70 of the balloon 44 are sealed to the outer sheath 62 to be fluid-tight. It should be appreciated that the outer sheath 62 is removed within the medial area of the balloon 44. It should also be understood that the ends 70 of the balloon 44 are fluidly sealed across the probe 12 to prevent fluid flow from balloon 44 region into the probe 12 past the ends 70. Thus the balloon 44 is fluid-tight so that it can be inflated by injecting a fluid into it.

The overall length of the balloon 44 should be in the range of 0.5 inches, with the inflatable medial portion of the balloon 44 measuring about 0.25 inches. When deflated, the balloon 44 should have a diameter comparable to that of the probe tip 34.

The construction for inflating the balloon is illustrated by FIGS. 7 and 8. As shown in these figures, each balloon injection tube 50 has a cut-away portion 68 inside the balloon 44. For clarity of illustration, only one of the four balloon injection tubes 50 is shown inside the balloon 44 in FIG. 7. Each cut-away portion 68 is about 0.25 inches long and extends approximately halfway into its balloon injection tube 50.

The purpose of the balloon injection tubes 50 and their cut-away portions 68 is to provide a conduit for the injection of fluid, typically a saline solution, into the balloon 44 to inflate the balloon 44. The inflated balloon 44 is indicated diagrammatically by broken lines in FIGS. 7 and 8.

As shown in FIG. 7, each imaging fiber 54 is stretched into a reduced-diameter portion 72 within the balloon 44. For clarity of illustration, however, only one of the imaging fibers 54 is shown in the balloon 44 of FIG. 7. The reduced-diameter portion 72 is typically about 500 microns in diameter, which is a reduction from the 700-micron diameter of the imaging fibers 54 throughout the rest of the probe 12.

The reduced-diameter portion 72 of the imaging fibers 54 provides an increased flow path for the fluid from the balloon injection tubes 50 into the balloon 44. The greater flow path between the light-emitting fibers 60 and the imaging fibers 54 facilitates inflation of the balloon 44 with fluid. In addition, reducing the diameter of the imaging fibers 54 in this manner does not detract from the imaging capability of the imaging fibers 54.

Turning to FIGS. 9 through 12, the structure of the probe coupler 36 is described in detail. The probe coupler 36 has a front coupling portion 74 and a rear coupling portion 76.

Figure 12:
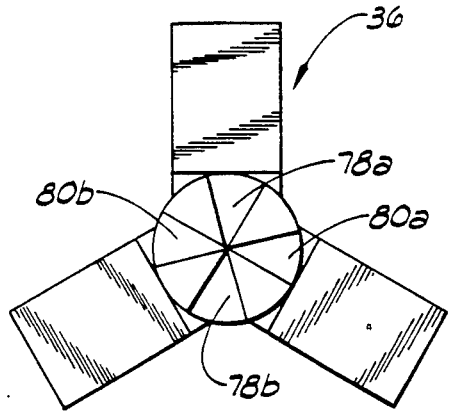
FIG. 12 is a front elevation of the probe coupler of FIG. 9.

The front coupling portion 74 is adapted for insertion into the aperture 39 of the E/M control assembly 14. As best shown in FIGS. 9 and 12, the front coupling portion 74 has two diametrically opposed wedge-shaped channels 78a and 78b which extend substantially throughout the length of the front coupling portion 74. In similar fashion, the front coupling portion 74 has two more diametrically opposed wedge-shaped channels 80a and 80b which extend partly into the front coupling portion 74.

Figure 10:
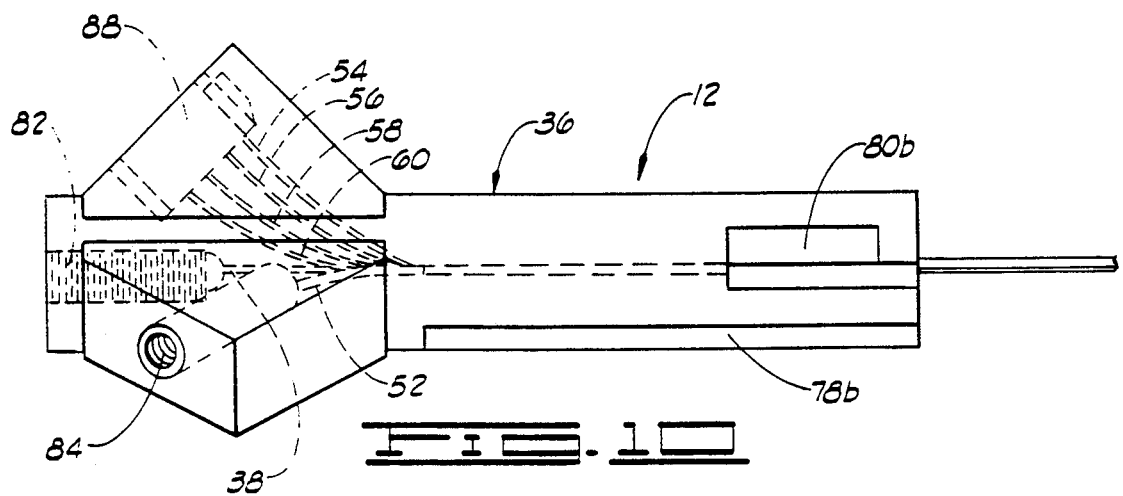
FIG. 10 is a side view of the probe coupler of FIG. 9.
Figure 11:
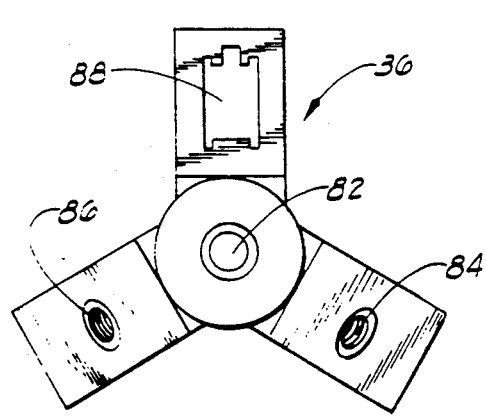
FIG. 11 is a rear elevation of the probe coupler of FIG. 9.

As shown in FIG. 10, the laser fiber 38, the fluid injection tubes 52, the balloon tubes 50, the light-emitting fibers 56, 58 and 60 and the imaging fibers 54 of the probe 12 extend into the rear coupling portion 76. The laser fiber 38 protrudes into a laser coupling 82, which is suitably adapted for attachment to the laser source 28.

The fluid injection tubes 52 extend into a fluid injection coupler 84, which is suitably adapted for attachment of fluid lines to the fluid injection system 20. Similarly, the balloon tubes 50 extend to a balloon tube coupler 86, which is suitably adapted for attachment of fluid lines to the balloon fluid system 18.

The imaging fibers 54 and the light-emitting fibers 56, 58 and 60 terminate into an optic fiber coupler 88 for connection to the imaging system 24 and light source 22, respectively. An optical index-matching gel with the same optical density as the fibers 54, 56, 58 and 60 may be used in the optic fiber coupler 88 to ensure a proper optical connection between the imaging system 24 and the light source 22 and the optical fibers 54, 56, 58 and 60.

With reference now to FIGS. 13 through 15, the E/M control assembly 14 is described in detail. There are two magnetic cores 90 and 92 in the E/M control assembly 14. The magnetic cores 90 and 92 are each configured to have two sets of coils or windings. As shown in FIG. 13, magnetic core 90 has windings L1 and L2, while magnetic core 92 is provided with windings L3 and L4.

Each magnetic core 90 and 92 also comprises a pair of wedge-shaped core members extending toward one another at a medial area of the magnetic core 90 and 92. The wedge-shaped core members of magnetic core 90 are designated by reference numerals 93 and 94, while the wedge-shaped core members of magnetic core 92 are designated by reference numerals 95 and 96.

The magnetic cores 90 and 92 are positioned to be perpendicular to one another with the wedge-shaped core members 93, 94, 95 and 96 forming a substantially straight line path for the insertion of the front coupling portion 74 of the probe coupler 36.

The windings L1, L2, L3 and L4 are wound onto the magnetic cores 90 and 92 in a manner to produce magnetic flux in the magnetic cores 90 and 92 when electric current is passed though the windings L1, L2, L3 and L4. In a typical embodiment, the windings L1, L2, L3 and L4 comprise insulated 18-AWG copper wire wrapped around the respective core 90 or 92 in 20 layers of 35 turns per layer. This particular configuration results in a total of 700 turns per winding.

The magnetic cores 90 and 92 themselves are made of "SUPERMALLOY," an alloy of nickel and iron which has extremely high magnetic permeability with low losses. As best illustrated by FIG. 15, the magnetic cores 90 and 92 are constructed by stacking a plurality of thin laminated plates of "SUPERMALLOY." This planar, laminated structure encourages longitudinal flow of magnetic flux within the magnetic cores 90 and 92 and discourages eddy flow of magnetic flux, that is, flow of magnetic flux in non-longitudinal directions.

The cores 90 and 92 are contained within a non-magnetic housing 100, diagrammatically designated by the inner square in broken lines of FIG. 13. Adequate support should be provided by the housing 100 to maintain the cores 90 and 92 in a rigidly stationary position. The housing 100 may be made of plastic, aluminum or any other suitable non-magnetic material.

If unshielded, the magnetic fields of the cores 90 and 92 interfere with one another. To reduce such interference, an inner shield housing 102, indicated diagrammatically by the outer broken lines in FIG. 13, is positioned around each winding L1, L2, L3 and L4 and its magnetic core area. Each inner shield housing 102 should be made of mumetal or a material having magnetic properties similar to mumetal.

In addition, a cylindrical outer shield housing 104 surrounds the entire assembly of magnetic cores 90 and 92 and windings L1, L2, L3 and L4. The outer shield housing 104 prevents magnetic interference of the device 10 with other instruments. Like the inner shield housing 102, the outer shield housing 104 is constructed of mumetal or a similar material. The outer shield housing 104 gives the E/M control assembly 14 the cylindrical shape shown in FIG. 1.

As previously mentioned, the E/M control assembly 14 has the aperture 39 adapted to receive the probe coupler 36. The spatial relationship of the control wires 42 and the wedge-shaped core members 93, 94, 95 and 96 of the magnetic cores 90 and 92 is illustrated diagrammatically by FIG. 14. For clarity, the tubes and fibers of the probe 12 are not shown in FIG. 14.

It should be appreciated that the control wires 42 are bare and exposed to the core members 93, 94, 95 and 96 within the aperture 39. There should be little or no air space separating each control wire 42 from its corresponding core member 93, 94, 95 or 96. The end of each wedge-shaped core member 93, 94, 95 and 96 is arcuate to conform with the round outer periphery of the corresponding control wire 42. When magnetized by an electric current through its winding L1, L2, L3 or L4, each core member 93, 94, 95 and 96 induces a magnetic field into the corresponding control wire 42.

It should also be understood that all four core members 93, 94, 95 and 96 are not positioned alongside the same portion of the control wires 42. As illustrated by FIG. 15, two opposing core members 93 and 94 are located at one section of the probe 12 and the other two opposing core members 95 and 96 are proximate to a neighboring portion of the probe 12.

Turning now to FIGS. 16 and 17, the joystick 32 and E/M control circuit 16 are described. As shown in FIG. 16, the handle of the joystick 32 may be moved up, down, right and left, as indicated by the reference characters S1, S2, S3 and S4. Of course, the joystick 32 may be moved in a wide variety of increments throughout a 360-degree range.

The E/M control circuit 16 shown in FIG. 17 is connected between the windings L1 and L2 of the magnetic core 90 and the joystick 32 to vary the electric current through the windings L1 and L2 in response to the position of the joystick 32. It should be appreciated that the circuit 16 controls the magnetic fields of only one pair of opposing core elements, namely core members 93 and 94, corresponding to the directions S1-S2.

An identical circuit (not shown) is provided to control the current through the windings L3 and L4, the magnetic fields in core members 95 and 96, and the S3-S4 directions. It should be understood that the movement of the magnetized sleeve 40 and laser fiber 38 is determined by the composite magnetic field resulting from all four control wires 42. Assuming current flow, each winding L1, L2, L3 and L4 produces a magnetic field which is a component of the composite magnetic field affecting the magnetized sleeve 40.

The upper half of FIG. 17 is the circuitry for controlling the current through winding L1. The left side of this circuitry provides positive current to the winding L1 and includes an N-channel JFET gate transistor 112, a 50KΩ variable resistor 114, a 100 μF capacitor 116, a 4-volt zener diode 118 and an NPN Darlington pair 120. The Darlington pair 120 typically used is RCA product no. SK3977/456 or an equivalent. The N-channel JFET 112 typically used is RCA product no. SK9161/457 or an equivalent.

The voltage across the capacitor 116 provides the bias voltage to the gate transistor 112 and the zener diode 118 ensures that the bias voltage does not exceed four volts. As the joystick 32 is moved in the S1-S2 direction, the variable resistance 114 is increased or decreased to change the bias voltage to the gate transistor 112. The change in bias voltage to the gate transistor 112 alters the current input to the Darlington pair 120, which in turn increases or decreases the current driving the winding L1.

The right upper portion of FIG. 17 provides negative current to the winding L1 and includes a P-channel JFET gate transistor 122 a 50KΩ variable resistor 124, a 100 μF capacitor and a PNP Darlington pair 130. The Darlington pair 130 may be RCA product no. SK3746/326 or an equivalent and the P-channel JFET 122 may be RCA product no. SK3746/326 or an equivalent. These components function in the same manner as that described for the left upper portion of FIG. 17, but produce a current flow in the opposite direction.

The emitters of the two Darlington pairs 120 and 130 are linked together. If Darlington pair 120 conducts more than Darlington pair 130, the current to the winding L1 is positive. On the other hand, if Darlington pair 130 conducts more than Darlington pair 120, the current to the winding L1 is negative. A resistor bridge 132 is provided between the current output and the winding L1 to limit the current to the winding L1.

An identical circuit, the lower half of FIG. 17, supplies current to the winding L2. It should be appreciated that S1-S2 movement of the joystick 32 affects the current in both windings L1 and L2 simultaneously. It should also be understood that the windings L1 and L2 produce opposite magnetic polarities in their respective core members 93 and 94. When core member 93 is "north" in polarity, core member 94 is "south." When core member 93 is "south," core member 94 is "north."

As mentioned previously, windings L3-L4 and core members 95 and 96 are associated with joystick 32 movement in the S3-S4 directions. It should be appreciated that circuitry identical to that for the L1-L2 windings is provided for the L3-L4 windings.

The E/M control circuit 16 is one current source which may be utilized with the device 10. It should be understood that any conventional current source which can be controlled with respect to current magnitude and direction may be used to perform the function of the E/M control circuit 16.

The amount of current required depends on the materials used and the size of the probe 12. As the effective diameter of the probe 12 and the diameter of the control wires 42 are made smaller, leakage flux increases and more current is generally required to compensate for the additional leakage flux.

OPERATION

The laser angioplasty device 10 is utilized in accordance with conventional angioplasty procedures. The probe tip 34 is inserted into the vascular system and guided radioscopically into the occluded vessel to the site of the occlusion. It should be appreciated that the control wires 42 and magnetized sleeve 40 are x-ray dense and, as such, facilitate radioscopic guidance of the probe tip 34 to the site of the occlusion.

After the probe tip 34 is positioned at the occlusion, the fluid injection system 20 is used to inject a transparent fluid, typically a saline solution, into the vessel between the probe tip 34 and the occlusion. It is desirable to achieve a mixture of about 90-percent saline solution and 10-percent erythrocytes in order to provide good visibility of the interior of the vessel and the occlusion.

Once the opacity of the blood is overcome, the light-emitting fibers 56, 58 and 60 and the imaging fibers 54 are able to provide visual images of the vessel and occlusion on the view screen 26 through the imaging system 24. By interactively viewing the video, the operator of the device 10 can steer the probe tip 34 into a position for ablating the occlusion.

It should be recalled that the laser light emitted from the laser fiber 38 is typically not visible, particularly in a white light produced by the light-emitting fibers 56. In order to see where the laser fiber 38 is aimed, a highly visible tracer light is emitted from the laser fiber 38.

At this point, it may be desirable to use the balloon fluid system 18 to inflate the balloon 44 for stabilizing the probe tip 34 in the vessel and for limiting blood flow around the probe 12 toward the occlusion.

Once again interacting with the video of the vessel and occlusion, the operator uses the joystick 32 to aim the tip of the laser fiber 38. The laser source 28 delivers a pulsed laser beam through the laser fiber 38 at the occlusion to ablate the occlusion. The operator is able to interact with the video to ensure that occlusion is fully vaporized and that normal tissue is not harmed.

After ablation of the occlusion, the balloon fluid system 18 is placed in vacuum mode to draw the fluid out of the balloon 44. With the balloon 44 deflated, the probe 10 is free to be withdrawn from the vessel and the vascular system.

Changes may be made in the combinations, operations and arrangements of the various parts and elements described herein without departing from the spirit and scope of the invention as defined in the following claims.

For example, the control wires 42 and magnetized sleeve 40 may be used to aim or steer a fiber, such as an optical fiber, rather than the laser fiber 38. Utilized with an optical fiber, the electromagnetic control capability described hereinabove may aim light or capture images at a wide variety of directions within a vessel.

What is claimed is:

1. A device for performing laser excision within a vessel, the device comprising:
    a laser fiber having a proximal end and a distal end, the distal end having a distal end portion with a laser fiber tip, the distal end portion of said laser fiber being insertable into a vessel;
    a magnetized sleeve disposed around the distal end portion of said laser fiber;
    laser means, operatively connected to the proximal end of said laser fiber, for emitting laser pulses from the laser fiber tip;
    a plurality of control wires insertable into the vessel with said laser fiber, each one of said control wires having a proximal end and a distal end, said control wires being spaced around said laser fiber with the distal end of each one of said control wires proximate to said magnetized sleeve;
    a plurality of magnetic cores, each one of said magnetic cores being located proximate to the proximal end of at least one of said control wires, said magnetic cores producing induced magnetic fields in the distal end of said control wires; and
    control means, operatively connected to said magnetic cores, for altering the magnetic fields in said cores;
    wherein the altering the magnetic fields in said magnetic cores alters the induced magnetic fields in the distal ends of said control wires and wherein altering the induced magnetic fields in the distal ends of said control wires alters the orientation of said magnetic sleeve to aim the distal end portion of said laser fiber.

2. The device of claim 1 further comprising:
    a laser tube having a proximal end and a distal end and circumscribing a medial portion of said laser fiber with the end portion of said laser fiber protruding from the distal end of said laser tube, substantially all of said magnetized sleeve being disposed outside the distal end of said laser tube, said control wires being disposed outside said laser tube, and the distal ends of said control wires being positioned at the distal end of said laser tube.

3. The device of claim 2 wherein said laser tube comprises nylon.

4. The device of claim 2 further comprising:
    an annular base attached to the inner periphery of said laser tube proximate to the end portion of said laser fiber.

5. The device of claim 4 wherein said annular base comprises stainless steel.

6. The device of claim 4 wherein said annular base comprises samarium cobalt.

7. The device of claim 4 wherein said annular base and said magnetized sleeve are magnetized to have opposite radial magnetic polarities.

8. The device of claim 1 further comprising: means for injecting a fluid wash into the vessel.

9. The device of claim 1 further comprising:
    means for producing a visually perceptible image of the interior of the vessel.

10. The device of claim 1 further comprising:

means for emitting light into the interior of the vessel.

11. The device of claim 1 wherein said magnetized sleeve comprises samarium cobalt.

12. The device of claim 1 wherein said laser fiber comprises silica.

13. The device of claim 1 wherein said laser fiber comprises a synthetic resinous material.

14. The device of claim 1 further comprising:
a balloon circumscribing the end portion of said laser fiber; and
means for inflating said balloon.

15. The device of claim 1 further comprising: an outer sheath circumscribing said laser fiber.

16. The device of claim 15 wherein said outer sheath comprises polytetrafluoroethene.

17. The device of claim 15 wherein said outer sheath has an outer periphery with a plurality of longitudinal runners.

18. The device of claim 17 wherein each of said runners has a rounded outer periphery.

19. The device of claim 1 wherein the distal end of said laser fiber extends reciprocatingly through said magnetic sleeve.

20. The device of claim 1 wherein the laser fiber tip is sized and shaped to prevent said magnetized sleeve from slipping off the distal end of said laser fiber.

21. A device for performing laser excision within a vessel, the device comprising:
a laser fiber having a proximal end and a distal end, the distal end having a distal end portion with a laser fiber tip, the distal end portion of said laser fiber being insertable into a vessel;
a magnetized sleeve disposed around the distal end portion of said laser fiber;
laser means, operatively connected to the proximal end of said laser fiber, for emitting laser pulses from the laser fiber tip;
a plurality of control wires insertable into the vessel with said laser fiber, each one of said control wires having a proximal end and a distal end, said control wires being spaced around said laser fiber with the distal end of each one of said control wires proximate to magnetized sleeve;
a plurality of magnetic cores located proximate to the proximal end of said control wires outside of the vessel, said magnetic cores being capable of inducing magnetic fields in the distal ends of said control wires;
circuit means, operatively connected to said magnetic cores, for producing and altering magnetic fields in said magnetic cores; and
a joystick operatively connected to said circuit means;
wherein movement of said joystick cooperates with said circuit means to alter the magnetic fields of said magnetic cores, wherein altering the magnetic fields in said magnetic cores alters the induced magnetic fields in the distal ends of said control wires, and wherein altering the induced magnetic fields in the distal ends of said control wires alters the orientation of said magnetized sleeve to aim the distal end portion of said laser fiber.

22. The device of claim 21 wherein said magnetic cores comprise iron and nickel.

23. The device of claim 21 wherein said magnetic cores are planar laminate.

24. The device of claim 21 further comprising: a shield housing surrounding said magnetic cores.

25. The device of claim 24 wherein said shield housing comprises mumetal.

26. The device of claim 2 wherein said laser tube is sized and shaped to prevent said magnetized sleeve from entering the distal end of said laser tube.

* * * * *